United States Patent
Adam et al.

(10) Patent No.: US 10,925,577 B2
(45) Date of Patent: *Feb. 23, 2021

(54) MULTIPLE APERTURE PROBE INTERNAL APPARATUS AND CABLE ASSEMBLIES

(71) Applicant: MAUI IMAGING, INC., San Jose, CA (US)

(72) Inventors: Sharon L. Adam, San Jose, CA (US); David M. Smith, Lodi, CA (US); Donald F. Specht, Los Altos, CA (US); Kenneth D. Brewer, Santa Clara, CA (US)

(73) Assignee: MAUI IMAGING, INC., San Jose, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 15/785,233

(22) Filed: Oct. 16, 2017

(65) Prior Publication Data

US 2018/0049717 A1  Feb. 22, 2018

Related U.S. Application Data

(63) Continuation of application No. 13/272,098, filed on Oct. 12, 2011, now Pat. No. 9,788,813.

(60) Provisional application No. 61/392,841, filed on Oct. 13, 2010.

(51) Int. Cl.
| | |
|---|---|
| A61B 8/00 | (2006.01) |
| A61B 8/12 | (2006.01) |
| G01S 7/52 | (2006.01) |
| G01S 15/89 | (2006.01) |
| G10K 11/00 | (2006.01) |

(52) U.S. Cl.
CPC .............. *A61B 8/12* (2013.01); *A61B 8/4477* (2013.01); *A61B 8/4483* (2013.01); *G01S 7/52079* (2013.01); *G01S 15/8915* (2013.01); *G01S 15/8927* (2013.01); *G10K 11/004* (2013.01); *G01S 7/52047* (2013.01)

(58) Field of Classification Search
CPC .................................................. A61B 8/4477
See application file for complete search history.

(56) References Cited

U.S. PATENT DOCUMENTS

| | | | |
|---|---|---|---|
| 2004/0267132 A1* | 12/2004 | Podany .................. | A61N 7/022 600/459 |
| 2005/0061536 A1* | 3/2005 | Proulx .................... | G06Q 10/08 174/102 R |
| 2009/0036780 A1* | 2/2009 | Abraham ................. | A61B 8/08 600/459 |

(Continued)

*Primary Examiner* — Rochelle D Turchen
(74) *Attorney, Agent, or Firm* — Shay Glenn LLP

(57) ABSTRACT

A Multiple Aperture Ultrasound Imaging (MAUI) probe or transducer is uniquely capable of simultaneous imaging of a region of interest from separate physical apertures of ultrasound arrays. The probe can include separate backing plates configured to secure the ultrasound arrays in predetermined positions and orientations relative to one another. Some embodiments of the probe include flex circuit connected to the ultrasound arrays. In additional embodiments, a flex/PC board comprising flex connectors and an array of terminals is connected to the ultrasound arrays. Algorithms can solve for variations in tissue speed of sound, thus allowing the probe apparatus to be used virtually anywhere in or on the body.

16 Claims, 17 Drawing Sheets

(56) References Cited

U.S. PATENT DOCUMENTS

2010/0036258 A1* 2/2010 Dietz .................. A61B 8/12
600/466
2010/0174198 A1* 7/2010 Young ................ A47C 27/144
600/484

* cited by examiner 1, 1.5, and 2 D Implementation using CMUT Material

Variable Cardiac Implementation

Fixed Cardiac Implementation

Omniplane Style TEE Implementation   FIG. 9
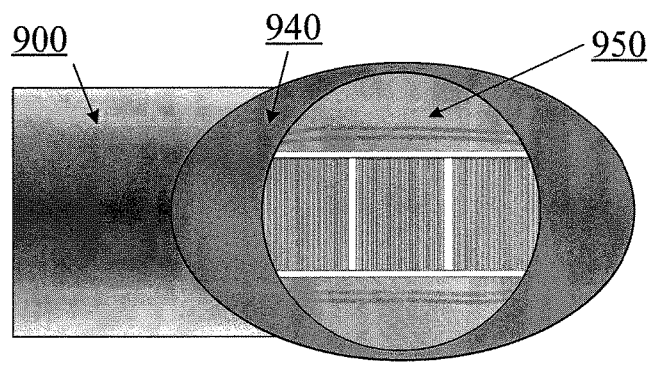
FIG. 9A
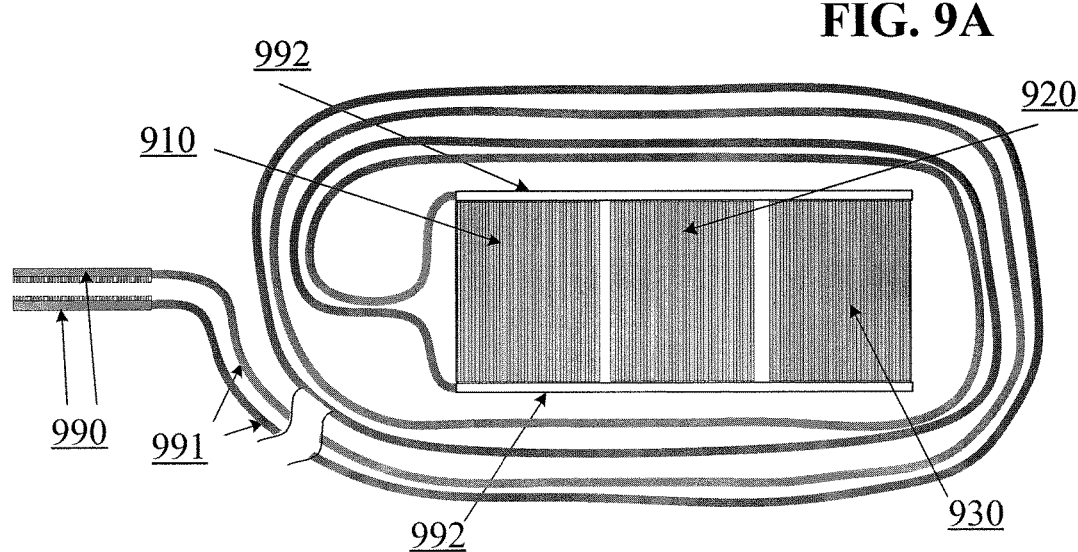
FIG. 9B
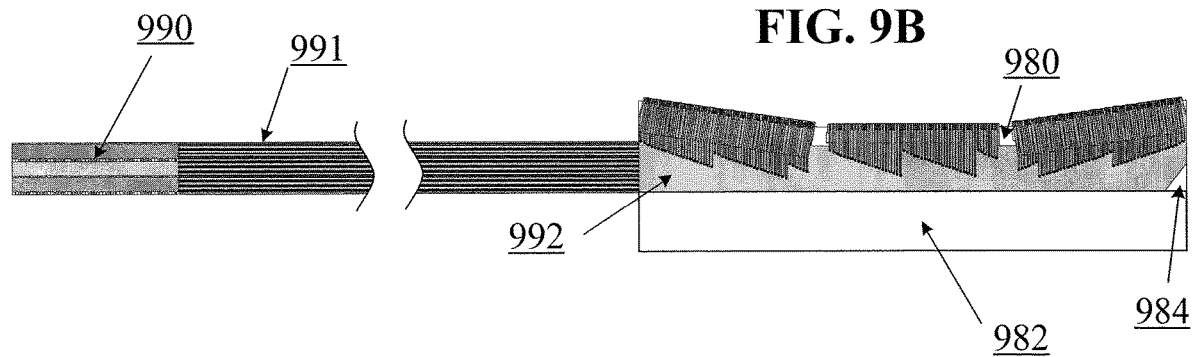

Intracavity Probe Implementation

IVUS Probe Implementation

MAUI 1 D Implementation using multiple Piezoelectric arrays

MULTIPLE APERTURE PROBE INTERNAL APPARATUS AND CABLE ASSEMBLIES

CROSS REFERENCE TO RELATED APPLICATIONS

This application is a continuation of U.S. application Ser. No. 13/272,098, filed Oct. 12, 2011, now U.S. Pat. No. 9,788,813, which application claims the benefit of U.S. Provisional Patent Application No. 61/392,841, filed Oct. 13, 2010, which applications are incorporated herein by reference.

This application is related to U.S. Pat. No. 8,007,439, issued Aug. 30, 2011, titled "Method and Apparatus to Produce Ultrasonic Images Using Multiple Apertures", U.S. patent application Ser. No. 12/760,375, filed Apr. 14, 2010, titled "Universal Multiple Aperture Medical Ultrasound Probe", U.S. patent application Ser. No. 13/002,778, filed Aug. 7, 2009, now U.S. Pat. No. 8,602,993, titled "Imaging with Multiple Aperture Medical Ultrasound and Synchronization of Add-On Systems", and U.S. patent application Ser. No. 12/760,327, filed Apr. 14, 2010, now U.S. Pat. No. 8,473,239, titled "Multiple Aperture Ultrasound Array Alignment Fixture".

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to imaging techniques, and more particularly to ultrasound imaging techniques, and still more particularly to an apparatus for producing ultrasonic images using multiple apertures.

BACKGROUND

In conventional ultrasonic imaging, a focused beam of ultrasound energy is transmitted into body tissues to be examined and the returned echoes are detected and plotted to form an image.

In order to insonify the body tissues, a beam formed either by a phased array or a shaped transducer is scanned over the tissues to be examined. Traditionally, the same transducer or array is used to detect the returning echoes. This design configuration lies at the heart of one of the most significant limitations in the use of ultrasonic imaging for medical purposes; namely, poor lateral resolution. Theoretically the lateral resolution could be improved by increasing the aperture of the ultrasonic probe, but the practical problems involved with aperture size increase have kept apertures small and lateral resolution large. Unquestionably, ultrasonic imaging has been very useful even with this limitation, but it could be more effective with better resolution.

In the practice of cardiology, for example, the limitation on single aperture size is dictated by the space between the ribs (the intercostal spaces). For scanners intended for abdominal and other use (e.g., intracavity or intravenous), the limitation on aperture size is a serious limitation as well. The problem is that it is difficult to keep the elements of a large aperture array in phase because the speed of ultrasound transmission varies with the type of tissue between the probe and the area of interest. According to Wells (Biomedical Ultrasonics, as cited above), the transmission speed varies up to plus or minus 10% within the soft tissues. When the aperture is kept small, the intervening tissue is, to a first order of approximation, all the same and any variation is ignored. When the size of the aperture is increased to improve the lateral resolution, the additional elements of a phased array may be out of phase and may actually degrade the image rather than improving it.

With single aperture transducers, it has been commonly assumed that the beam paths used by the elements of the transducer are close enough together to be considered similar in tissue density profile, and therefore no compensation was necessary. The use of this assumption, however, severely limits the size of the aperture that can be used.

SUMMARY

Multiple aperture ultrasound probes may be constructed with unique cable assemblies, multiple flex connectors, and unique backing plate constructions, and unique electrical connections to reduce noise and improve the quality of images produced using multiple aperture ultrasound imaging techniques. The embodiments provided herein allow for effective mechanical and electrical connection of ultrasound transducer elements and arrays to probes and imaging control electronics.

In one embodiment, a multiple aperture ultrasound probe is provided, comprising a probe housing containing a first ultrasound array and a second ultrasound array, a first flex circuit connected to the first ultrasound array, a second flex circuit connected to the second ultrasound array, a backing plate configured to secure the first and second ultrasound arrays in predetermined positions and orientations relative to one another, a first coaxial cable group electrically connected to the first flex circuit, a second coaxial cable group electrically connected to the second flex circuit, and a flex/PC board comprising flex connectors and an array of terminals, wherein said flex connectors are connected to said first and second flex circuits, and wherein said terminals are connected to said first and second coaxial cable groups.

In some embodiments, the first and second ultrasound arrays comprise a plurality of transducer elements, wherein each element is connected to the flex/PC board with a differential pair of conductors having a signal ground separated from a chassis ground.

In one embodiment, the backing plate is electrically connected to chassis grounding circuitry via the transducer cable shield originating at an electronic control system. In another embodiment, the backing plate internally supports the probe structure.

In some embodiments, the multiple aperture ultrasound probe further comprises a calibration chip mounted on the flex/PC board. In some embodiments, the calibration chip is configured to store position and orientation information about the first and second ultrasound arrays.

In some embodiments, the multiple aperture ultrasound probe further comprises a probe position sensor mounted on the flex/PC board.

In another embodiment, the multiple aperture ultrasound probe further comprise a synchronization module mounted on the flex/pc board, the synchronization module being configured to synchronize an add-on ultrasound device with the first and second ultrasound arrays.

In one embodiment, the multiple aperture ultrasound probe further comprises a third ultrasound array secured to the backing plate, a third flex circuit connected to the third ultrasound array, a third coaxial cable group electrically connected to the third flex circuit, wherein flex connectors of the flex/PC board are connected to the third flex circuit and terminals of the flex/PC board are connected to the third cable group.

In one embodiment, the flex/PC board comprises a probe chassis ground circuit that is electrically connected to a shielding element surrounding a section of the first and second cable group bundles between the probe housing and a distal connector.

In another embodiment, at least one of the first array and the second array comprises an internal flex cabling configured to accommodate movement of the first ultrasound array away from the second ultrasound array.

In some embodiments, the probe further comprises a sliding portion configured to allow the first ultrasound array and the second ultrasound array to move laterally relative to the probe housing.

In one embodiment, at least one of the first ultrasound array and the second ultrasound array is configured to rotate about an axis of the probe housing.

In additional embodiments, the probe housing further comprises a lever configured to move the first ultrasound array or the second ultrasound array relative to the probe housing.

In some embodiments, the probe housing further comprising a dial and an electric motor configured to move the first ultrasound array or the second ultrasound array relative to the probe housing.

BRIEF DESCRIPTION OF THE FIGURES

FIG. 9 illustrates an embodiment of a multiple aperture omniplane transesophogeal (TEE) multiple aperture probe using three or more arrays.

FIG. 9A is a top view of the arrays of the probe of FIG. 9, including associated cabling without the encasement.

FIG. 9B illustrates a side view of the probe of FIG. 9 multiple aperture illustrating individual arrays secured by a backing plate.

DETAILED DESCRIPTION

Multiple aperture ultrasound imaging probes may be substantially improved by providing unique cable assemblies, flex connectors, and backing blocks and other components to improve ultrasound signal quality and overall imaging performance. For example, unique backing blocks may be configured to maintain a desired geometry between adjacent elements and arrays that may not be attached to each other via a common substrate. Further, some embodiments of common substrates may be shaped in such a way that additional mechanical support systems provide substantial benefits. Systems and methods for effectively connecting ultrasound transducer elements and arrays both mechanically and electronically in multiple aperture probes are shown and described herein.

Embodiments of multiple aperture ultrasound imaging (MAUI) probes and methods of using them to obtain high resolution ultrasound images are shown and described in Applicants' prior US patent applications, which are referenced above.

Figure 2:
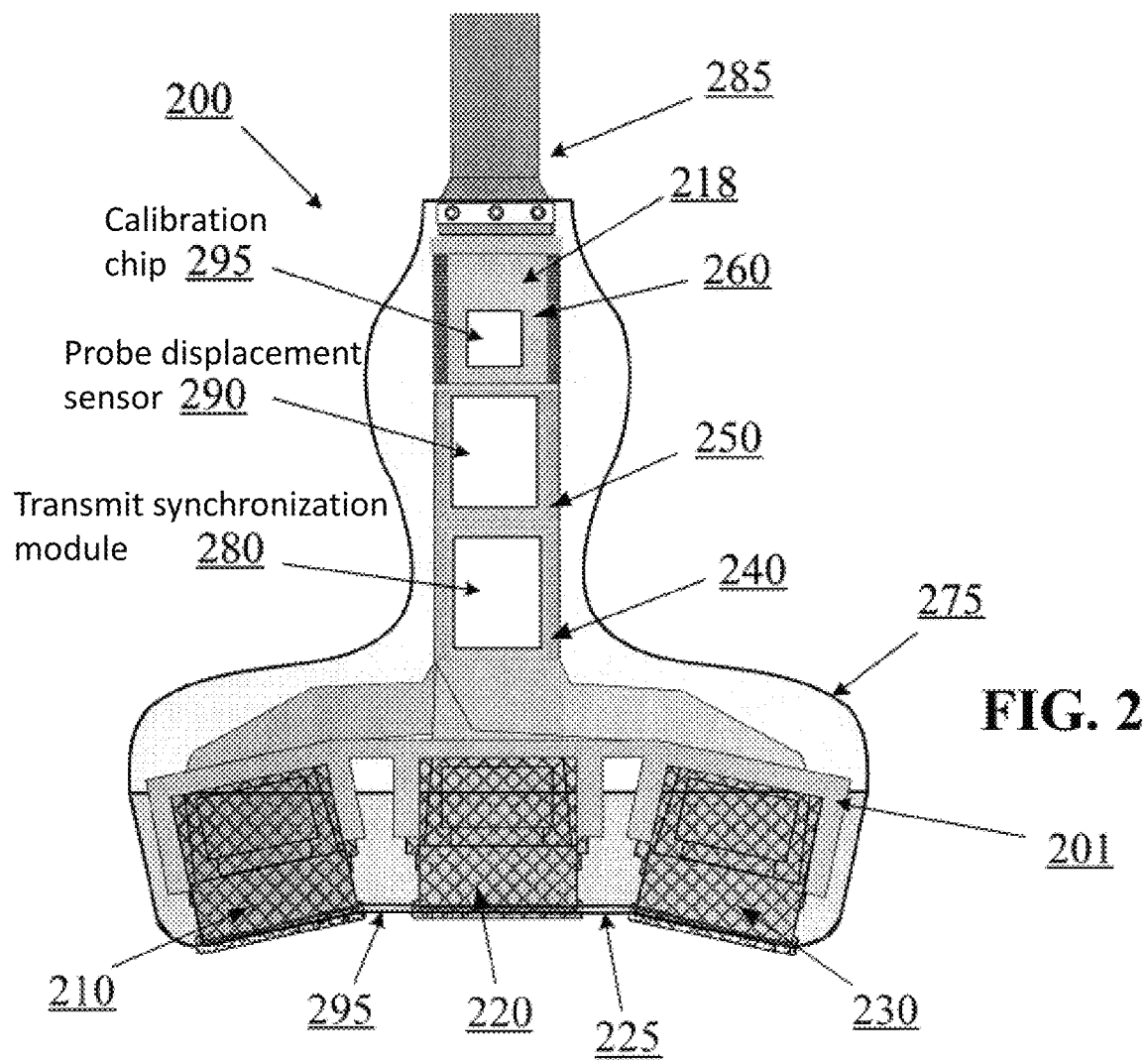
FIG. 2 is an elevation view of one embodiment of a multiple aperture ultrasound probe with a top housing section removed to reveal components therein.
Figure 7:
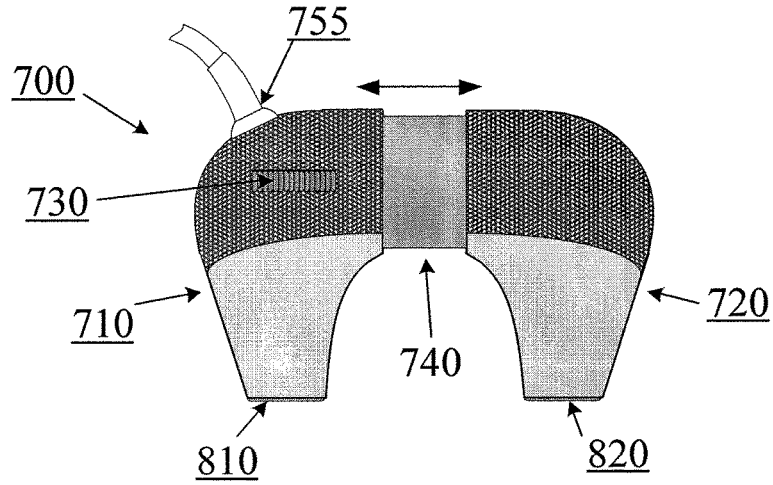
FIG. 7 illustrates an embodiment of an adjustable, extendable two-array multiple aperture probe in a partially extended configuration.
Figure 7A:
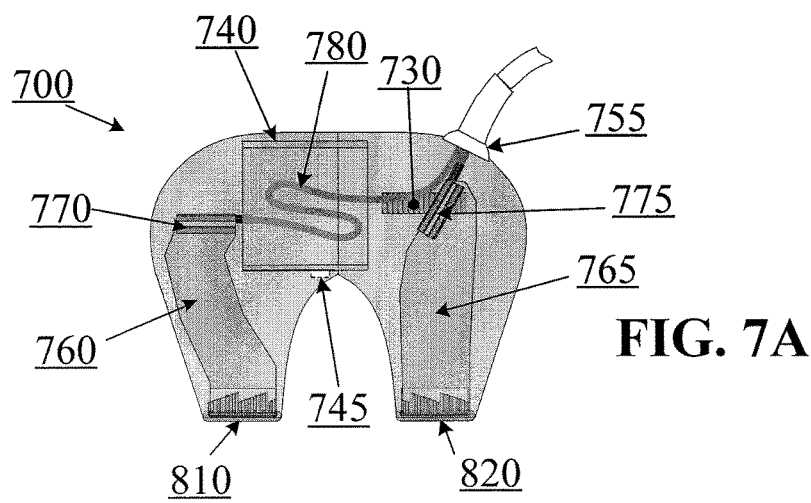
FIG. 7A is a side view of the probe of FIG. 7 in a collapsed configuration with internal components visible.

As described in the above-referenced patents and applications, the structure of a MAUI Probe can vary substantially to meet the needs of a particular application. For example, a general radiology probe (an embodiment of which is shown in FIG. 2) may contain multiple arrays that maintain separate physical points of contact with the patient's skin, allowing multiple physical imaging apertures. A cardiac probe (an embodiment of which is shown in FIG. 7) may contain as few as two arrays allowing the probe to fit simultaneously between two or more intercostal spaces. An intracavity version of a MAUI probe (an embodiment of which is shown in FIGS. 9-9B), may have arrays positioned along the length of a wand, while an intravenous MAUI probe (an embodiment of which is shown in FIG. 13) may allow the arrays to be located on the distal length the catheter and separated by mere millimeters. In each of these application-specific probe embodiments, a plurality of transducer arrays may be positioned and contained by a single backing plate configured to support each of the arrays in a desired position at a desired specified angle relative to the other arrays of the probe. Details of the angle and position of probes may depend on the intended function of a probe.

As used herein the terms "ultrasound transducer" and "transducer" may carry their ordinary meanings as understood by those skilled in the art of ultrasound imaging technologies, and may refer without limitation to any component capable of converting an electrical signal into an ultrasonic signal and/or vice versa. For example, in some embodiments, an ultrasound transducer may comprise a piezoelectric device. In other embodiments, ultrasound transducers may comprise capacitive micromachined ultrasound transducers (CMUT).

Ultrasound transducers are often configured in arrays of multiple individual transducer elements. As used herein, the terms "transducer array" or "array" generally refers to a collection of transducer elements mounted to a common substrate. Such arrays may have one dimension (1D), two dimensions (2D), 1.5 dimensions (1.5D) as understood by those skilled in the art. Other dimensioned arrays as understood by those skilled in the art may also be used. Transducer arrays may be made from piezoelectric materials, CMUT materials or any other suitable material. An element of a transducer array may be the smallest discretely functional component of an array. For example, in the case of an array of piezoelectric transducer elements, a single element may be a single piezoelectric crystal or a single machined section of a piezoelectric crystal. A transducer array may include any number of individual transducer elements as needed. Thus, in some embodiments an array may include a single element, and in other embodiments an array my include hundreds of elements. Unless specified otherwise for a particular embodiment, the embodiments herein may use any suitable ultrasound transducer array.

As used herein, the term "aperture" refers to a conceptual "opening" through which ultrasound signals may be sent and/or received. In actual practice, an aperture is simply a group of transducer elements that are collectively managed as a common group by imaging control electronics. For example, in some embodiments an aperture may be a physical grouping of elements which may be physically separated from elements of an adjacent aperture. For example, each of the three transducer arrays in the probe of FIG. 2 may be treated as a separate aperture. However, adjacent apertures need not necessarily be physically separated.

In some embodiments, two apertures may be located adjacent one another on a continuous array. In other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below.

Figure 1:
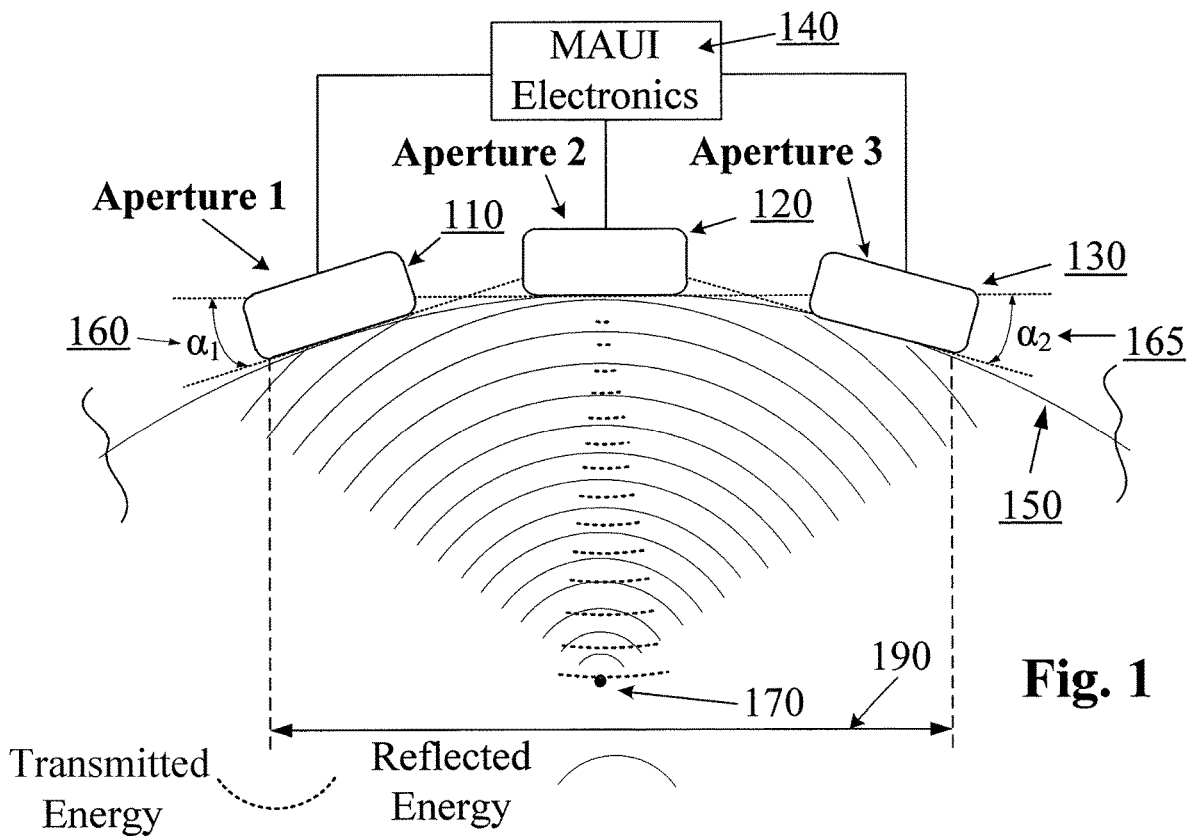
FIG. 1 is a block diagram illustrating one embodiment of transmit and receive functions of a Multiple Aperture Ultrasound Imaging (MAUI) probe.
Figure 1A:
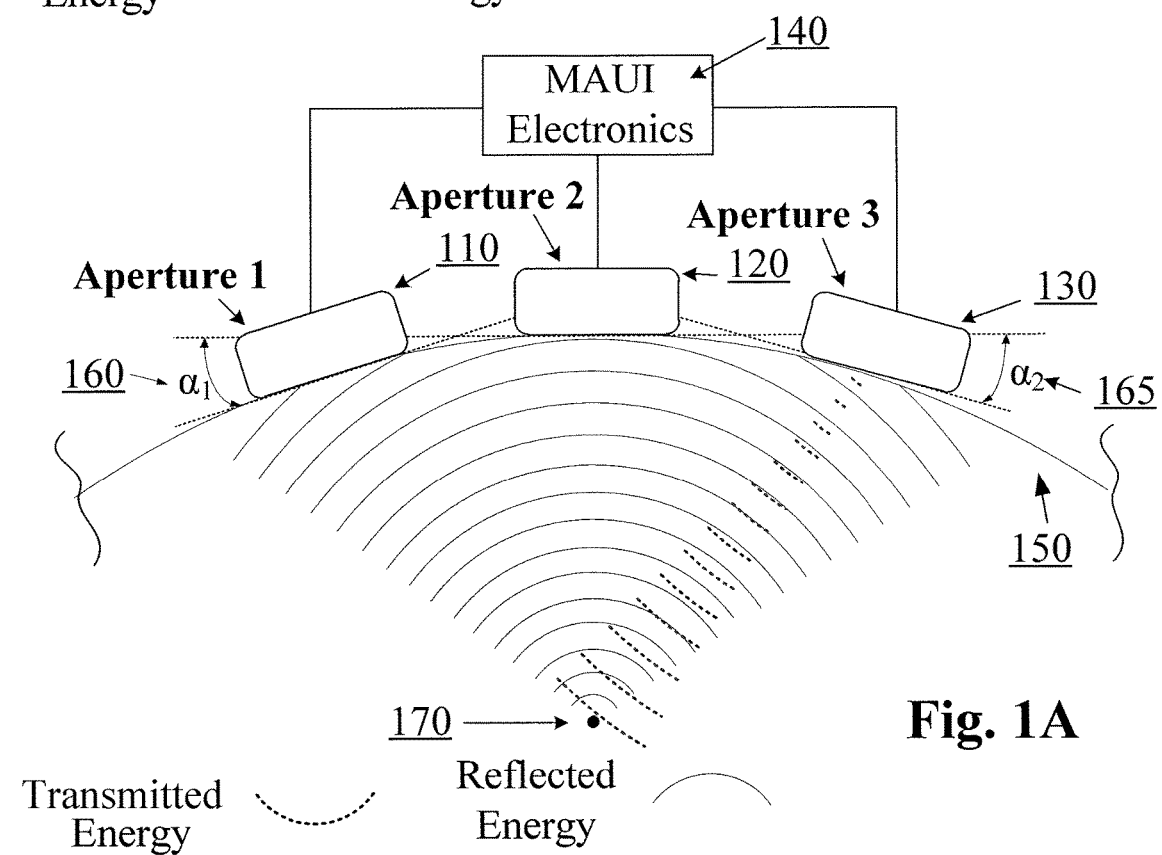
FIG. 1A is a block diagram illustrating additional functions of a multiple aperture ultrasound imaging system.

FIGS. 1 and 1A provide schematic illustrations of a multiple aperture ultrasound imaging process. Control electronics 140 may be provided to control the physical function of elements located within the different apertures 110, 120, and 130 of a Multiple Aperture Ultrasound Probe. FIGS. 1 and 1A demonstrate that in some embodiments, transmissions from two different apertures 120 in FIGS. 1 and 130 in FIG. 2 can be used to illuminate a target 170, while elements in all apertures 110, 120 and 130 can all be used for receive beamforming.

In some embodiments, a multiple aperture ultrasound imaging probe may be calibrated to precisely determine the acoustic position of each transducer element of each array. Embodiments of systems and methods for calibrating an ultrasound probe are provided in U.S. patent application Ser. No. 12/760,327. Thus, while calibration may allow for the use of complex arrays and probes (including adjustable probes), it is desirable that the transducer elements and arrays remain in the same physical position between calibration and use of a probe.

Some embodiments of multiple aperture ultrasound probes have several of the distinguishing features illustrated in FIG. 2. For example, the probe 200 of FIG. 2 includes three transducer arrays 210, 220 and 230, which are physically separated from one another and oriented at different "look angles" with respect to a region of interest to be imaged. While the probe 200 of FIG. 2 includes three transducer arrays, the features and advantages of the embodiments herein may be realized with probes having any number of independent transducer arrays, including arrays with non-planar shapes.

Figure 4:
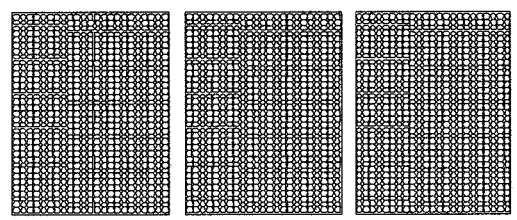
FIG. 4 illustrates an embodiment of 1D, 1.5d or 2D arrays for use in a 3-array multiple aperture ultrasound probe.
Figure 4:
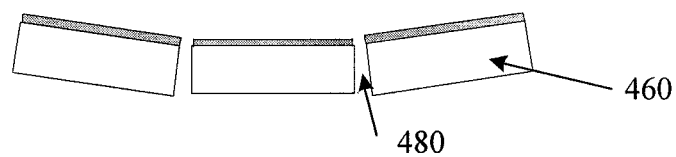
Figure 4A:
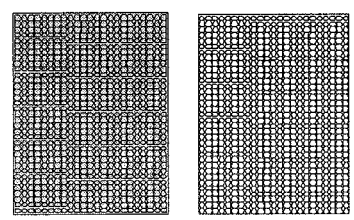
FIG. 4A illustrates an embodiment of a 2-array multiple aperture transducer array.
Figure 4A:
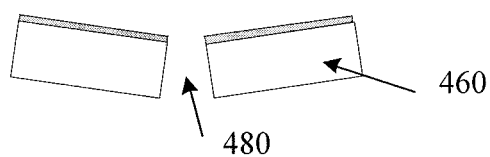

In some embodiments, each array may be constructed with a separate substrate or backing block (e.g., see 460 in FIGS. 4 and 4A). The backing block may be configured to structurally support the elements of an array in a desired shape (e.g., a planar shape). Backing blocks may be made of any substantially rigid material, such as metals, plastics, ceramics, etc. In some embodiments, a probe with multiple arrays may include arrays that all have the same shape and dimensions. In other embodiments, a probe with multiple arrays may include arrays that all have different shapes and/or dimensions. For example, one or more arrays in a multiple-array probe may be circular, elliptical, oblong, rectangular, square, polygonal or other symmetrical or asymmetrical shapes. In some embodiments, a probe with multiple arrays may include one or more arrays that are entirely or partially configured to transmit and/or receive ultrasound signals of a different frequency than other arrays in the probe.

Spacing between arrays (e.g., see 480 in FIGS. 4 and 4A) may vary, and need not be evenly distributed across a probe. In some embodiments, arrays may be arranged symmetrically or asymmetrically in a probe.

Referring back to FIG. 2, a probe may also include a transmit synchronization module 280 for identifying the start of pulse in certain applications. In some embodiments, a probe displacement sensor 290 may also be included within a probe housing. In some embodiments, the probe displacement sensor 290 may be an accelerometer or gyroscope configured to sense the three dimensional movement of the probe. In some embodiments, a calibration chip 295 may also be provided in the probe housing. In further embodiments, additional electrical or electronic components may also be included within the probe housing.

In some embodiments, a plurality of arrays within a single probe, such as the three arrays 210, 220, 230 in the probe of FIG. 2, may share a common backing plate 201 that is configured to secure the arrays in a designed position and orientation relative to one another and relative to the probe housing.

In the embodiment of FIG. 1, the angle $\alpha_1$ 160 is the angle between a line parallel to the elements of the left array 110 and an intersecting line parallel to the elements of the center array 120. Similarly, the angle $\alpha_2$ 165 is the angle between a line parallel to the elements of the right array 130 and an intersecting line parallel to the elements of the center array 120. Angle $\alpha_1$ and angle $\alpha_2$ need not be equal. In some embodiments, there are benefits in achieving optimum beamforming if the two angles 160, 165 are nearly equal.

FIG. 2 illustrates an embodiment of a MAUI probe 200 having three transducer arrays mounted in a housing 275 at static or pre-set mechanical positions and angles relative to one another and relative to the probe housing 275. The lateral arrays 210, 230 may be fixed at a desired position and angle, $\alpha$, relative to the central array 220 by attaching all three arrays 210, 220, 230 onto a single backing plate 201.

In some embodiments, as shown in FIG. 2 for example, the lateral arrays 210, 230 may both be positioned at an angle $\alpha$ of about 12.5° relative to the central array 220. In some embodiments, the angle $\alpha$ may be varied in order to optimize a probe for a particular imaging application. In other embodiments, the angle $\alpha$ of one or both lateral arrays relative to a central array may vary within a range of values to optimize imaging performance at different depths.

For a scatterer at a given depth, the effective aperture of a substantially planar lateral array is proportional to the sine of the angle between a line from the scatterer to the center of the lateral array and a line on the surface of the array itself. For example, with the lateral arrays positioned at an angle $\alpha$ of about 12.5°, the effective aperture of the lateral sub arrays is optimized at a depth of about 10 cm from the tissue surface, which may be beneficial when imaging cardiac features. Thus, in some embodiments, the angle $\alpha$ may be chosen as the best compromise for tissues at a desired depth range.

Figure 2A:
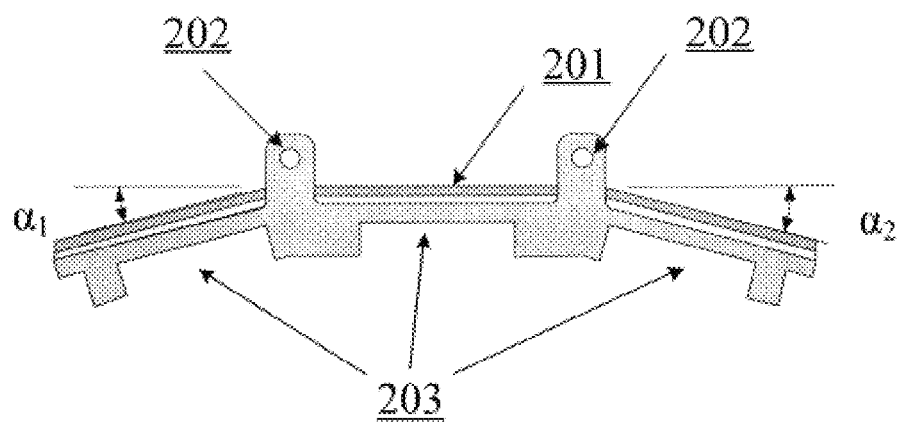
FIG. 2A illustrates one embodiment of a backing plate for securing multiple transducer arrays in predetermined positions and orientations with respect to each other within the probe housing.

FIG. 2A illustrates an embodiment of a backing plate 201 which may be used to mount three arrays into a multiple aperture ultrasound probe housing, such as that shown in FIG. 2. In some embodiments, the backing block may be configured to support lateral transducer arrays at an angle $\alpha$ relative to the central array. In some embodiments, the backing plate 210 may include slots 203 for receiving and retaining the backing blocks 460 of transducer arrays.

The backing plate 201 may be constructed by any suitable manufacturing process including machining, stamping, forging, casting, molding, 3D printing, etc. In some embodiments, the backing plate 201 may be constructed with sufficiently strict tolerances that array backing blocks fit snugly within the slots 203. In some embodiments, array backing blocks may be secured to the backing plate 201 with mechanical fasteners, adhesives, press fits or any other suitable method.

In some embodiments, transducer arrays may be manufactured with electrical contacts exposed on one or more side surfaces of the array and/or backing block material. A flex circuit may be electrically connected to those contacts. In such embodiments, the backing plate 201 may be configured to leave such array electrical contacts exposed so as to allow flex circuits to be electrically connected to the arrays. For example, the backing plate 201 may include one or more slots, channels or openings to accommodate such electrical connections. In other embodiments, a backing plate 201 may include one or more connectors configured to electrically connect array elements to corresponding flex circuit conductors while keeping the array element connections insulated from the backing block.

In some embodiments, the backing plate 201 may include one or more ribs in order to provide additional mechanical rigidity without necessarily adding weight to the probe. The backing plate 201 may also include any number of mounting flanges 202 or other structures configured to allow the backing plate 201 to be secured to one or more probe housing components. In some embodiments, the backing plate 201 may be secured to a probe housing shell 175 with mechanical fasteners, adhesives, press fits, or other methods. In some embodiments, a backing plate 201 may be formed integrally with a probe housing component.

In some embodiments, the backing plate 201 may also be used to complete a separate electrical grounding circuit, which will be referred to herein as a chassis ground. A chassis ground circuit, which will be discussed in more detail below, may extend from the backing plate, through a cable, through a connector and to an ultrasound imaging control/display system.

Figure 2B:
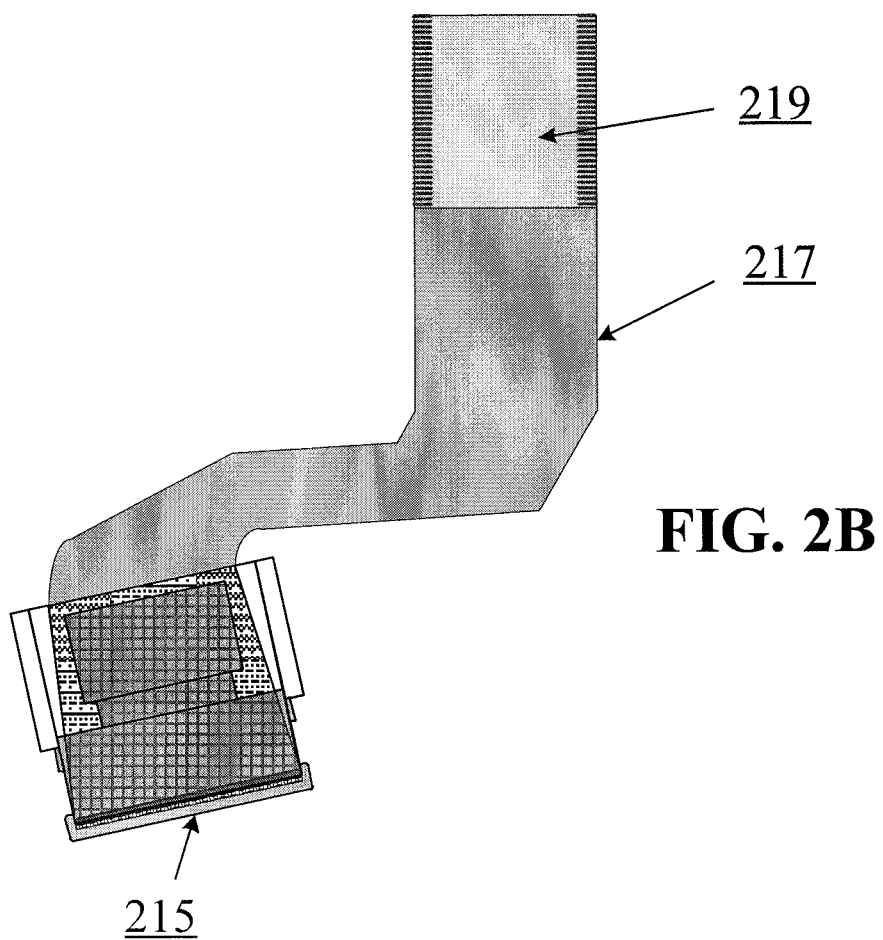
FIG. 2B is a diagram of one embodiment of a flex circuit attaching directly to an ultrasound transducer array.

In some embodiments, as shown in FIG. 2B, a lens 215 may be provided at a front surface of each transducer array. In some embodiments, a second common lens may be provided in front of each of the multiple arrays. In some embodiments, the individual lenses, or a single common lens may form a seal with the probe housing 275 to prevent coupling gel or other liquids from getting inside of the probe. In some embodiments, the front surfaces of the lenses of arrays 210, 220, and 230 may combine with the probe encasement 275 to form a substantially continuous concave arc.

In some embodiments, a multiple aperture ultrasound probe 200 may be a handheld apparatus that operates at a location remote from a base unit system configured to send and receive ultrasound signals. In some embodiments, communication between a multiple aperture probe and a base unit system may be performed through a cable that both mechanically and electrically connects the probe to a base unit system (or systems) configured to send and receive ultrasound signals. In some embodiments, it is advantageous to provide separate cabling and connections to each of the arrays or individual elements within a probe assembly.

Figure 3:
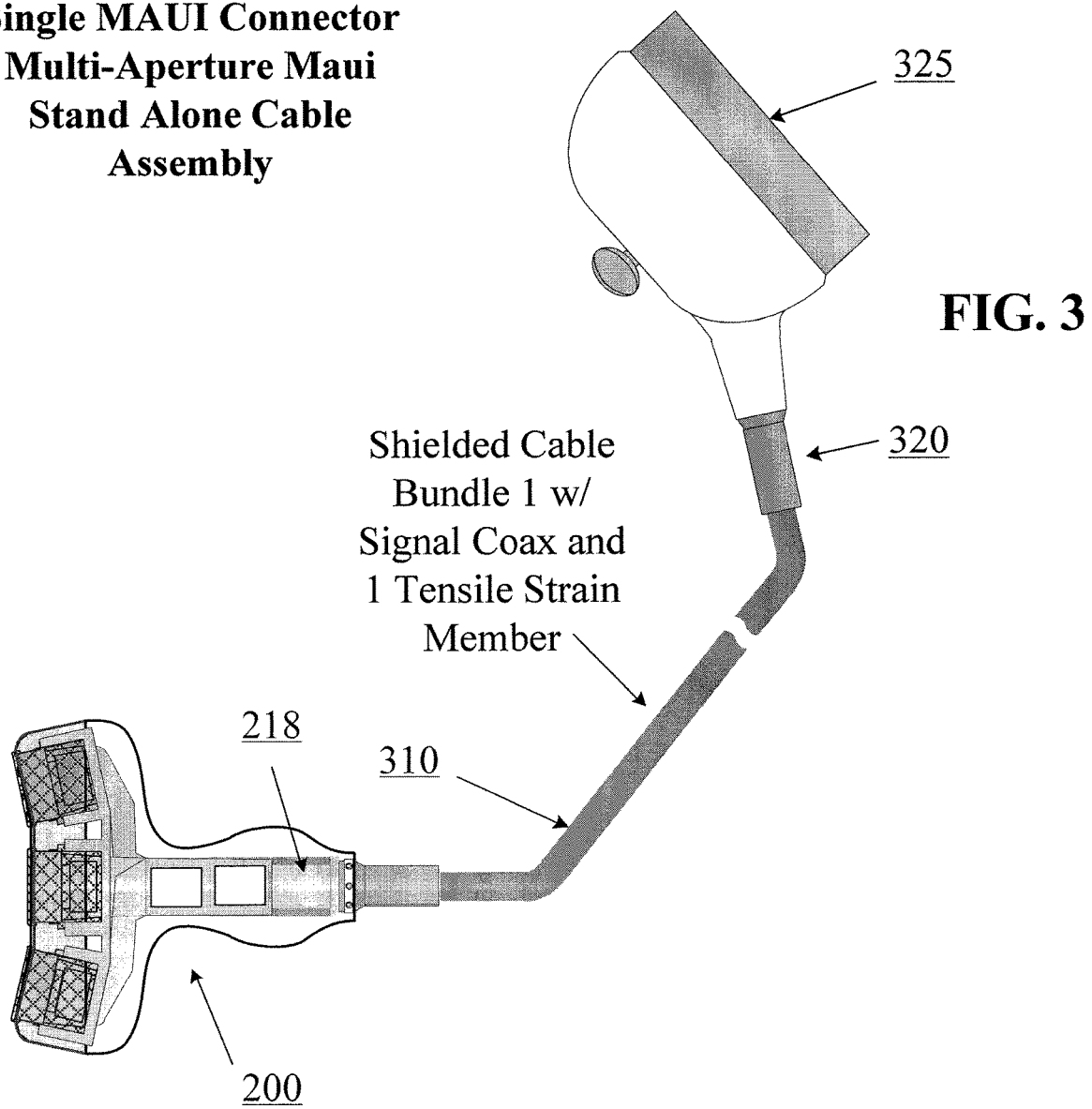
FIG. 3 illustrates an embodiment of a multiple aperture probe, cable and connector assembly.

FIG. 3 illustrates a multiple aperture ultrasound probe 200 including a cable 310 and connector 325. In some embodiments, strain relief elements 320 may be provided at junctions where the cable 310 connects to the connector housing and the probe housing. In some embodiments, the cable 310 is electrically connected to a flex/PC board 218 (examples of such connections are discussed below with reference to FIG.

2D). In some embodiments, the cable 310 may comprise a shielded construction in which a continuous conductor (e.g., a braid or thin foil) surrounds a bundle of individual conductors.

In some embodiments, the bundle of conductors may include a plurality of coaxial cables, which are themselves individually shielded. In some embodiments, the cable bundle may also include coaxial conductors that may be electrically connected to additional electronic components within the probe housing, such as a probe displacement sensor 290, a calibration chip 295 and/or a synchronization module 280.

In some embodiments, the cable may also include a tensile strain relief member, such as a steel cable (or other high tensile strength and low stretch material) configured to carry substantially an entire mechanical tensile load applied between the probe 200 and the connector 325.

In some embodiments, cable arrangements within a multiple aperture imaging probe may be uniquely configured for high quality transmission of electronic signals between each individual transducer element and an imaging control system (e.g., MAUI electronics or another host control system). In some embodiments, each transducer element may be electrically connected to an imaging control system with a unique differential pair of conductors. Such arrangements substantially reduce difficulties caused by cross-talk and other forms of electrical and/or electromagnetic interference.

In some embodiments, a probe may also be provided with a separate chassis ground circuit that is separate from any of the individual element grounds. In some embodiments, the chassis ground circuit may also be electrically connected to a shielding conductor surrounding other conductors in a cable bundle extending from the probe to a connector. An imaging control system may be configured to join the shield ground to a true earth ground. In some embodiments, an interior surface of a probe housing may also include a continuous electrically conductive layer for providing further shielding.

Figure 2C:
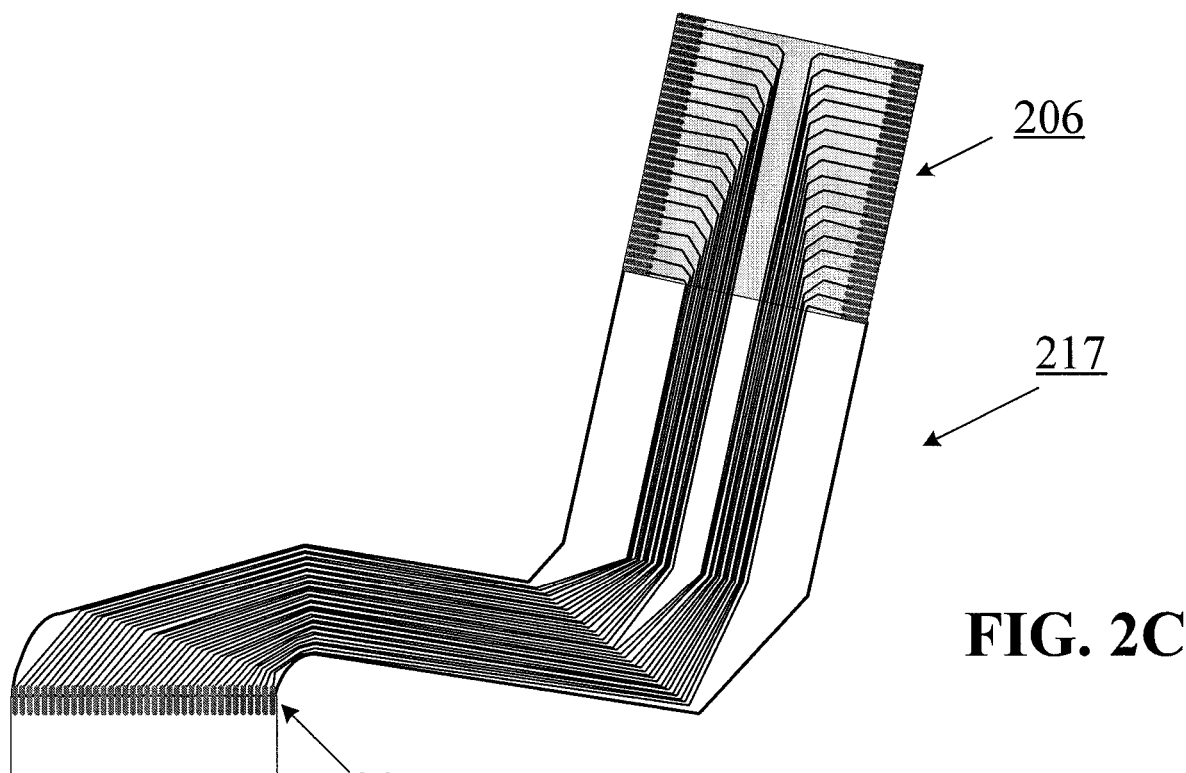
FIG. 2C is a diagram of one embodiment of a flex circuit for electrically connecting a single transducer array to probe electronic circuits.
Figure 2C:
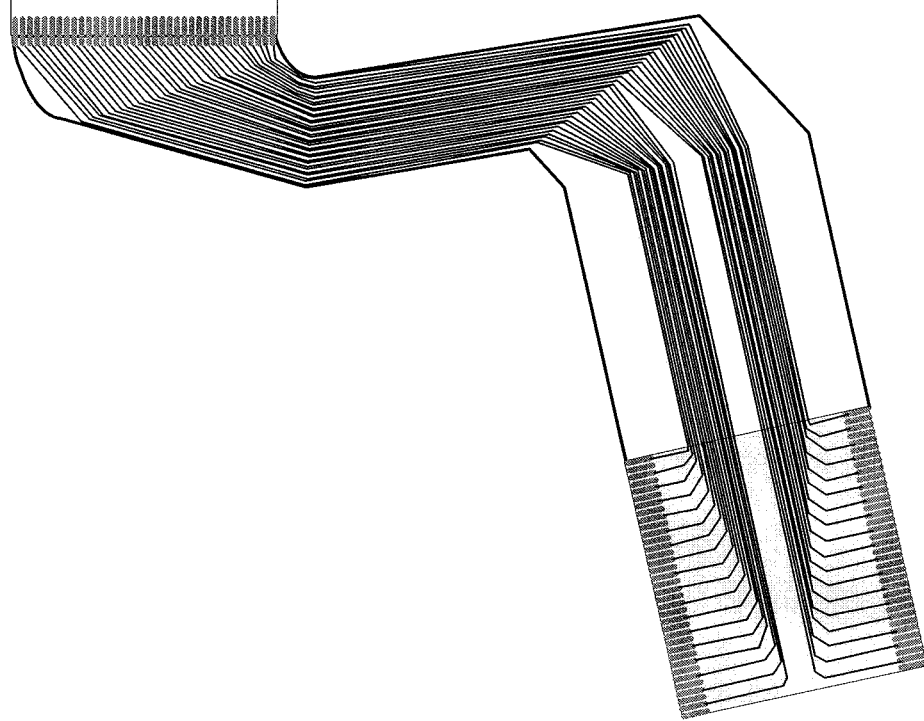

FIGS. 2B and 2C illustrate an embodiment of a unique flex circuit 217 for electrically connecting a transducer array to a flex/PC board 218 which may be further connected to a cable. In some embodiments, a flex circuit 217 may provide a differential pair electrical connection from each element of a transducer array to a terminal end 219. FIG. 2B illustrates a circuit 217 with an element-connection end connected to a backing block of a transducer array. FIG. 2C illustrates a two-sided flex circuit 217 with two rows of element connectors 205 configured to be electrically connected to elements of a transducer array. The element connectors 221 of the flex circuit 217 may be electrically connected to the array's elements either in manufacturing or after via surface mount connectors, surface solder joints or any other suitable method. In alternative embodiments, individual cables may be used in place of flex circuits for electrically connecting transducer array elements to a PC board or directly to a cable.

Figure 2D:
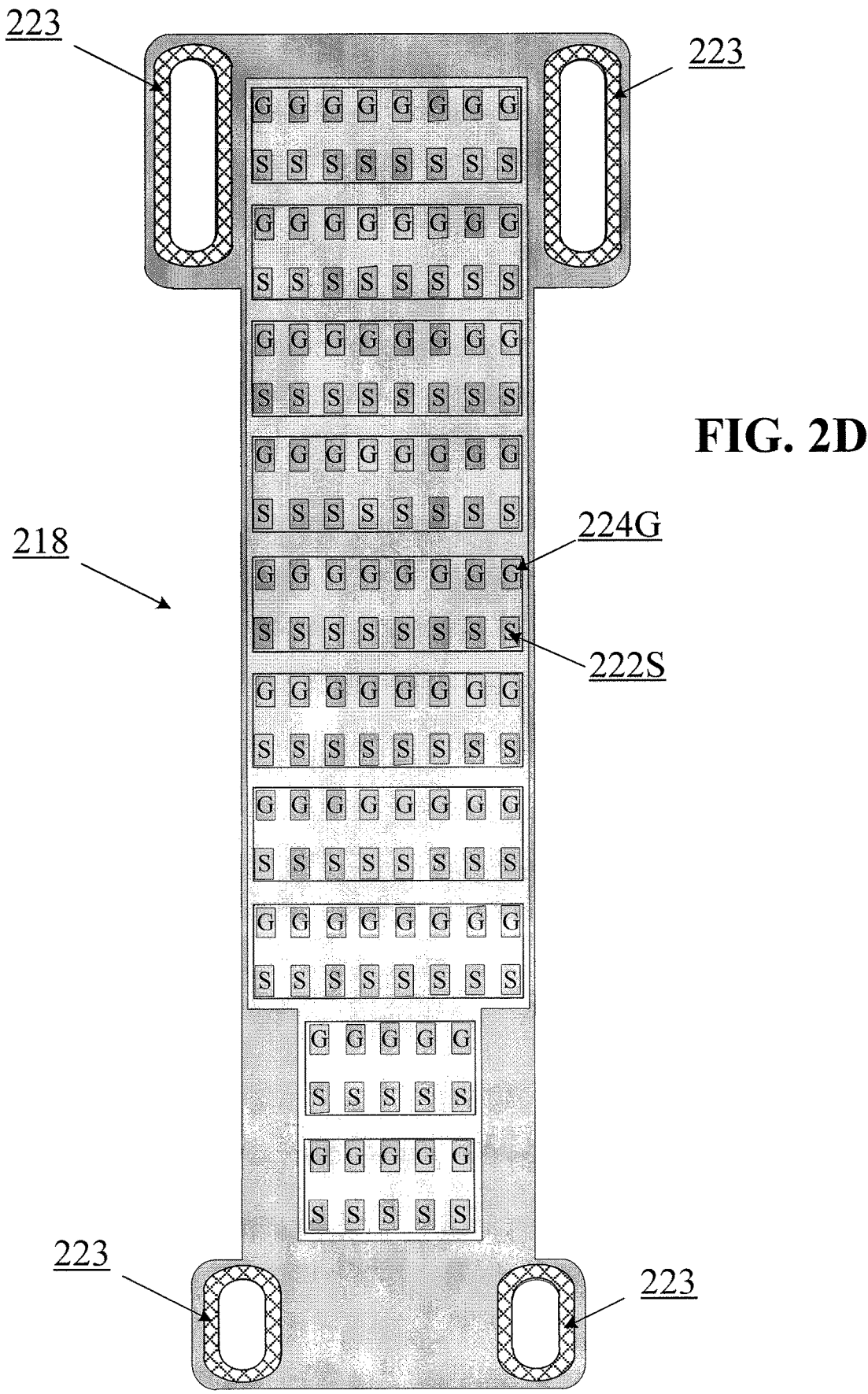
FIG. 2D is a diagram of one embodiment of a flex/PC board that may provide electrical connections between flex circuits and coaxial cables.
Figure 2E:
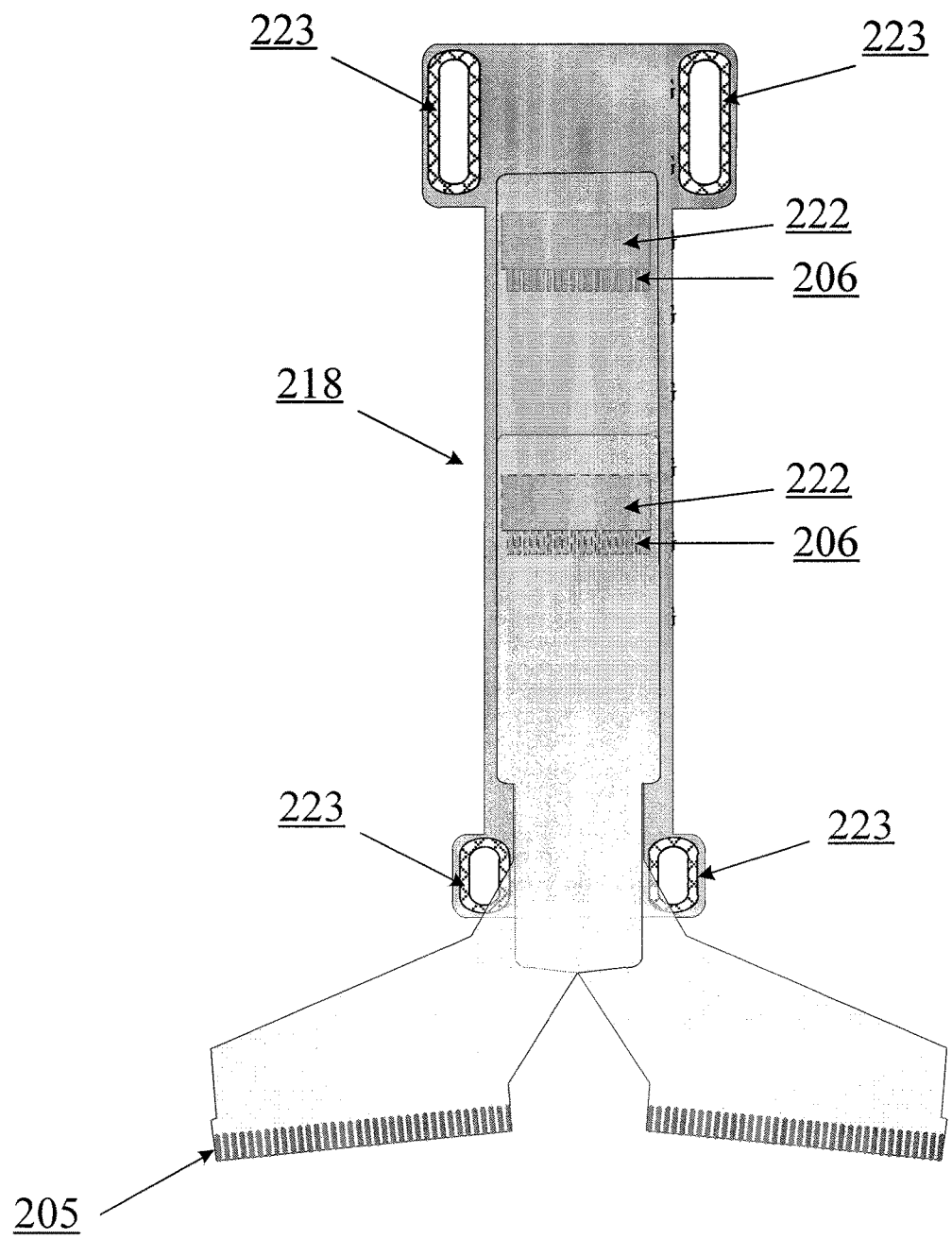
FIG. 2E is a diagram illustrating an embodiment of multiple custom flex circuits terminating onto a flex/PC board.

In some embodiments, the terminal end 219 of a flex circuit 217 may include an array of connectors 206 configured to be connected to corresponding flex terminal connectors 222 on a first side of the flex/PC board 218. FIG. 2E illustrates the flex connector side of the flex/PC board 218 with a pair of flex circuits 217 connected to a flex/PC board 218. In some embodiments, a flex/PC board 218 may be a substantially rigid printed circuit board with one or more flex terminal connectors 222 on one face, and an array of cable terminals on the opposite face. In some embodiments, circuit conductors may be printed into the board to provide electrical connections between flex circuit conductors and corresponding cable terminals. The flex/PC board 218 may also include grounding pads 223 which may be electrically connected to the chassis ground circuit.

In some embodiments, a flex/PC board 218 may be configured to keep the signal coaxial cables grounded separately from the chassis and/or outer cable shielding ground. FIG. 2D illustrates an array of connection terminals on the cable-connector side of the flex/PC board 218. As shown, the array of connections may include rows of ground terminals 224G paired with rows of signal terminals 224S.

Figure 2F:
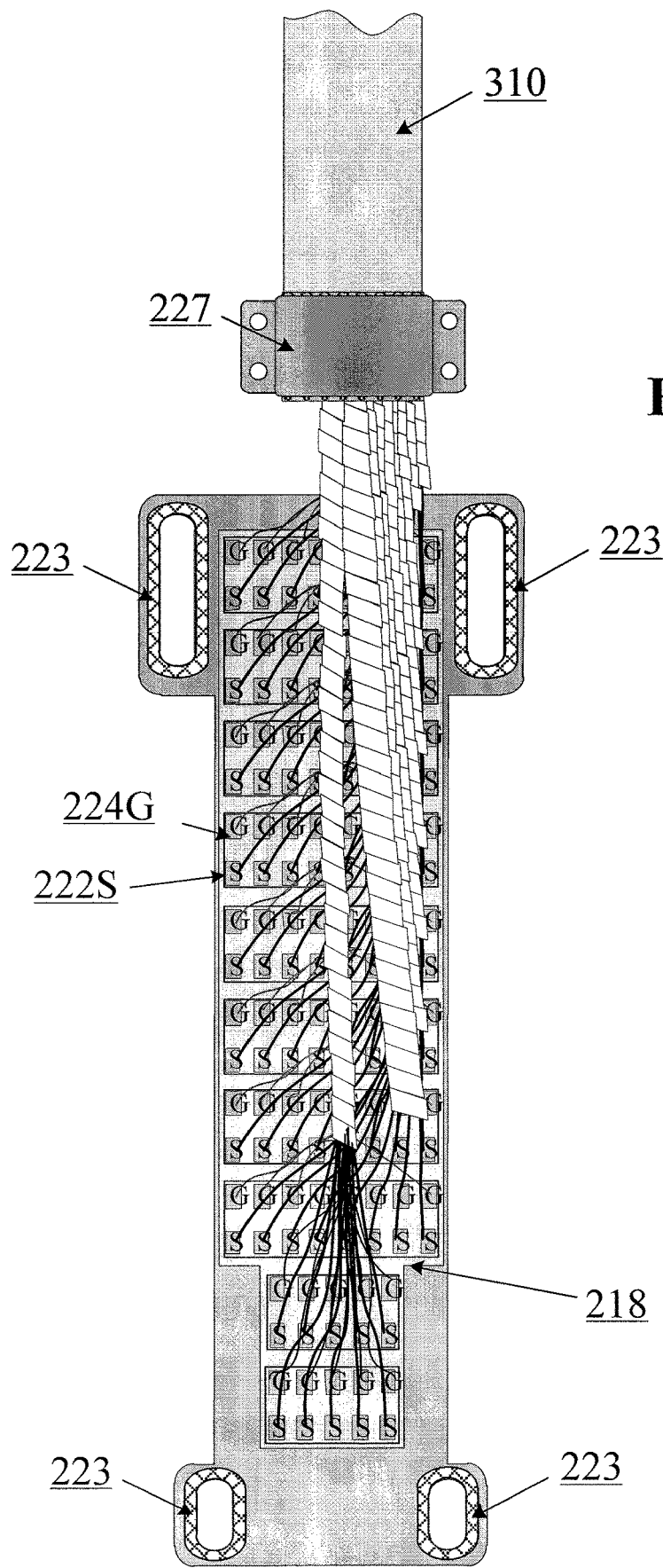
FIG. 2F is a diagram illustrating an embodiment of connections between bundles of coaxial cables and a flex/PC board.

FIG. 2F illustrates the connections of the individual coaxial cables from the cable bundle 310 to individual element-specific terminals on the flex/PC board 218. Each coaxial cable in the cable bundle may include an outer insulator, a shield conductor, an inner insulator and a central conductor. The central conductor may be referred to as the signal conductor, because it normally carries the electrical signals from the imaging control system to the transducer elements and back. In some embodiments, coaxial cables may be micro-coaxial cables (or "microcoax" cables), which may be about 42 gauge to about 58 gauge (or about 0.0025 inches to about 0.00039 inches in diameter).

In some embodiments, the signal conductor of each coaxial cable may be soldered to a corresponding signal terminal 224S, and the shield conductor of the same coaxial cable may be soldered to a corresponding ground terminal 224G. Thus, in some embodiments, there is no electrical path from a particular signal ground to any other signal ground. Similarly, embodiments may be configured such that no signal ground has an electrical path to the common chassis ground.

In some embodiments, coaxial cable conductors may be soldered directly to the contacts of the flex/PC board 218. In other embodiments, various mechanical connectors or clamps may alternatively be used. In further embodiments, any other wiring harness or connector may be used as desired.

As shown in FIG. 2F, a cable clamp 227 may also be provided to provide mechanical and/or electrical connection to the probe housing. In some embodiments, the cable clamp 227 may be electrically connected to the chassis ground tabs 223. In some embodiments, the cable clamp 227 may also be mechanically connected to the flex/PC board or directly to the probe housing. The cable clamp may also provide a mechanical attachment for a tensile strain relief element of the cable.

In some embodiments, a flex/PC board may also be configured to perform other functions by including additional integrated circuit chips soldered or otherwise electrically connected to the board.

In some embodiments, the flex/PC board may be used to re-task elements to either transmit or receive functions, such as by using dynamic electronic switching arrangements, or by configuring the connection of coaxial cables to terminals in varying arrangements.

In some embodiments, the flex/PC board may be used to arbitrate signals so that fewer cables are required in the bundles. For example, in some embodiments, a single coaxial cable may be electrically connected to the contacts of more than one transducer element (e.g., by using jumpers to connect selected terminals 224). In other embodiments, electronic switches may be provided on the flex/PC board to allow for dynamic switching of the relationship between a transducer element and a coaxial cable. Thus, in some embodiments, a cable bundle 310 may include fewer cable pairs than the number of individual transducer elements, while still providing substantial benefits of connecting elements with differential conductor pairs.

In other embodiments, the flex/PC board may include components configured to arbitrate signals for transmission to imaging control electronics via one or more fiber optic cables. For example, electrical to fiber optic conversion components and fiber optic coupling components may be mounted to the flex/PC board in order to convert electrical signals from the transducer elements into optical signals to be transmitted to an imaging control system via a fiber optic cable bundle in place of the coaxial cable bundle 310.

In alternative embodiments, all coaxial cables may be omitted, and a wireless communications chip may be provided in the probe housing and configured to communicate with an ultrasound imaging control system wirelessly. In some embodiments, such a wireless communications chip may be based on one or more common wireless data transmission standards, such as the IEEE 802.11 standards (e.g., "WiFi"), IEEE 802.15 standards (e.g., "Bluetooth") or others. A wireless communications chip may be soldered or otherwise connected to a flex/PC board which may also include flex connectors electrically connected to flex circuits connected to transducer arrays.

Figure 5:
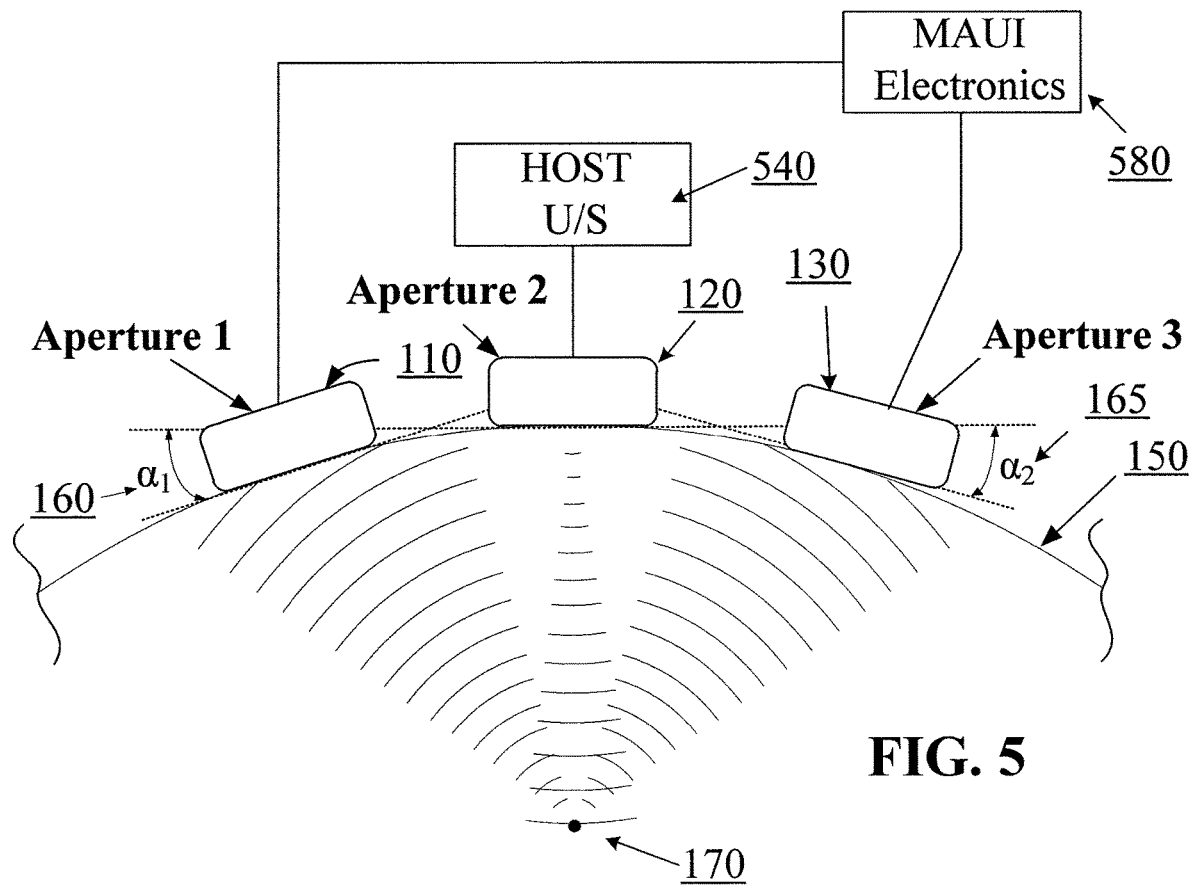
FIG. 5 is a block diagram illustrating an embodiment of transmit and receive functions for a Multiple Aperture Ultrasound probe connected to a host ultrasound system and a separate add-on control system.
Figure 5A:
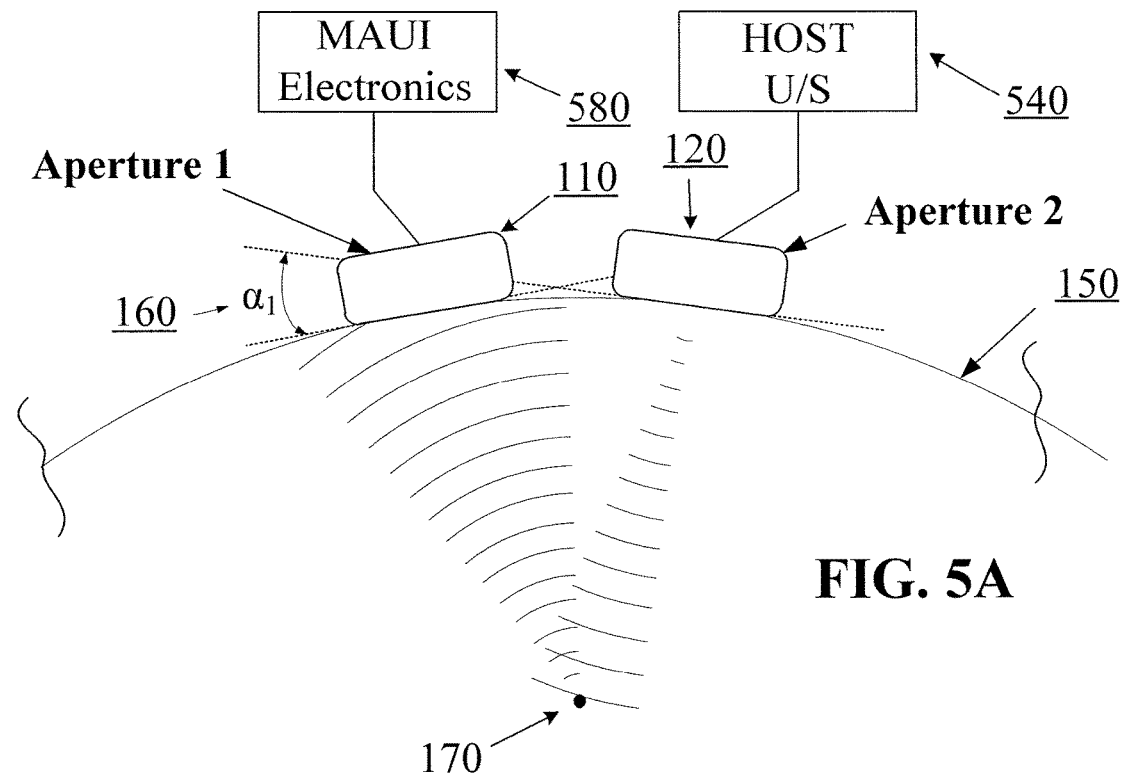
FIG. 5A is a block diagram illustrating an embodiment of transmit and receive functions for a Multiple Aperture Ultrasound probe used in a two array format.

Some embodiments of multiple aperture probes can also be constructed to operate as add-on devices to any ultrasound imaging host system, even those not specifically configured to operate multiple aperture probes. FIGS. 5 and 5A provide block diagrams illustrating two multiple aperture ultrasound imaging operations utilizing a standard host ultrasound system and a multiple aperture ultrasound imaging add-on device. In the example of FIG. 5, the center array 120 may be used for transmit only. The lateral arrays 110 and 130 may be used for receive only. The embodiment of FIG. 5A demonstrates the right array 120 being used to transmit, and the left array 110 being used to receive ultrasound signals.

Figure 6:
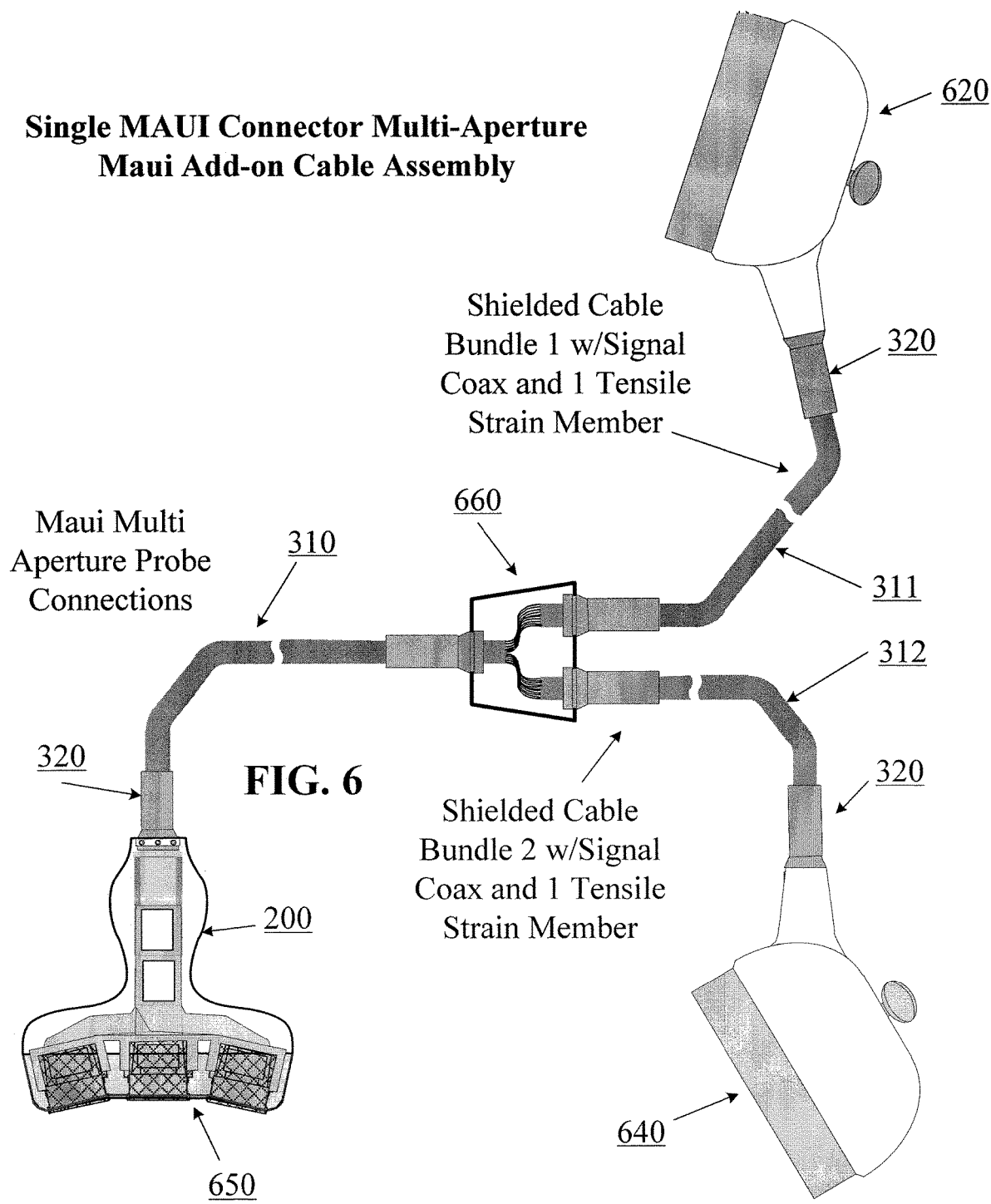
FIG. 6 illustrates an embodiment of a multiple aperture probe, cable and connector assembly configured for connection to both a host ultrasound imaging control system and an add-on imaging control system.

FIG. 6 illustrates an embodiment of a three-array multiple aperture probe 200 with cables and connectors for using the probe with an add-on system. Such a system may include substantially similar construction discussed above from the probe 200 to the junction box 660. From the junction box, the bundle of coaxial cables may be divided into a first cable branch 311 with a first connector 620 and a second branch 312 with a second connector 640. The first connector 620 may be configured to be attached to a host ultrasound system which provides transmit energy to the transmit array. The second connector 640 may be configured to connect to a stand-alone MAUI electronics system configured to receive and interpret echoes to generate images. Like the single system, the add-on system cabling coming from the multiple aperture probe may be bundled together so as to provide ease of use and maneuverability for an operator. In some embodiments, cable junction boxes 660 and strain reliefs 320 may be used on all cables.

FIGS. 7-13A provide several additional embodiments illustrating examples of multiple aperture ultrasound probe construction and cable assemblies. These examples represent some of the possible application-specific multiple aperture probes that may be constructed. Many variations in size and layout of each of the probes described herein are also possible.

Figure 7B:
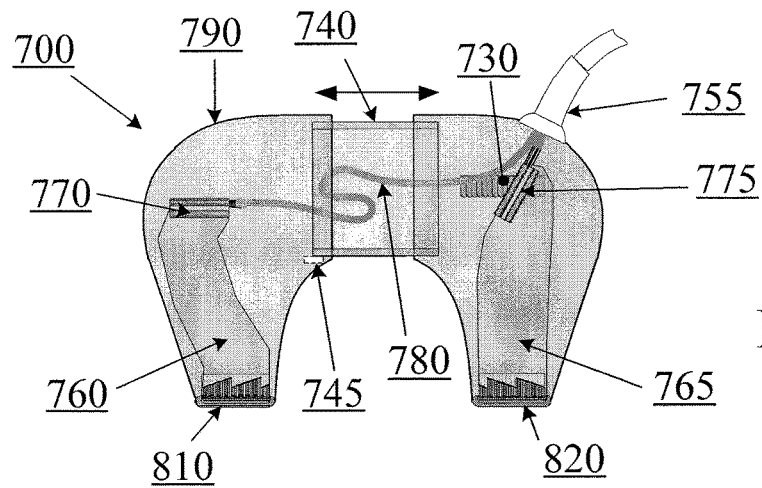
FIG. 7B shows the probe of FIG. 7A in an extended configuration with internal components visible.

FIGS. 7-7B illustrate an embodiment of a multiple aperture probe 700 having a design and features that make it particularly well suited for cardiac applications. As illustrated in FIG. 7, some embodiments of a multiple aperture probe 700 may include a pair of legs 710, 720 joined by a common central portion 740. In the embodiment of FIG. 7, the central body portion 740 is configured to allow the legs to slide relative to one another. Each leg portion 710, 720 may include a transducer array 810, 820 respectively on a lower surface.

In some embodiments, a sensor 775 can be provided on or adjacent to the slidable central portion 740. Such a sensor can be configured to transmit mechanical position information of each of the legs 710, 720 back to the MAUI electronics. Suitable sensors may include optical sensors, digital encoders, potentiometers or any other suitable sensor.

The embodiment in FIG. 7 illustrates a thumb wheel 730 that may be used to physically adjust the position of the legs 710, 720. In alternative embodiments, any other mechanism or device may be provided to control size adjustment of the probe.

In the illustrated embodiment, one leg of the probe 710 may encase one flex circuit 760, and the other leg 720 may encase a separate flex circuit 765. The flex circuits in these embodiments may be any of the types described above, Similarly to the embodiments above, the probe may include individual flex circuits 760, 765 in each leg 710, 720. The flex circuits may be attached via connectors to separate flex/pc boards 770, 775 configured with suitable shapes and sizes to fit within the probe housing. In some embodiments, the extender 740 section may enclose an extra length of coaxial cable bundles 780 as slack to accommodate adjustment of the legs. The cables may then be bundled together and inserted into strain relief 755.

Figure 8:
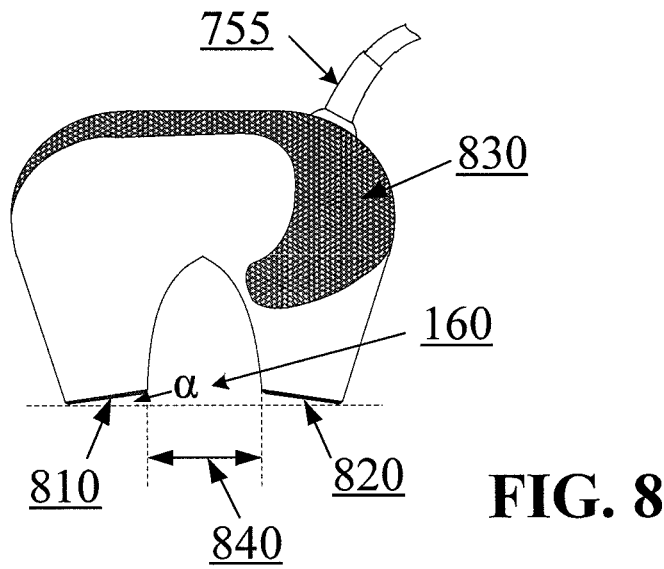
FIG. 8 illustrates an embodiment of a hand-held two-array multiple aperture probe with a non-adjustable fixed width.

FIG. 8 illustrates an embodiment of a fixed-position multiple aperture probe of similar shape to those shown in FIGS. 7-7B. The distance between the legs 840 may be fixed to be used in cardiac applications where it is desirable to "see" between or around ribs and through the intercostal spaces. Such probes may also be useful in other applications.

Figure 8A:
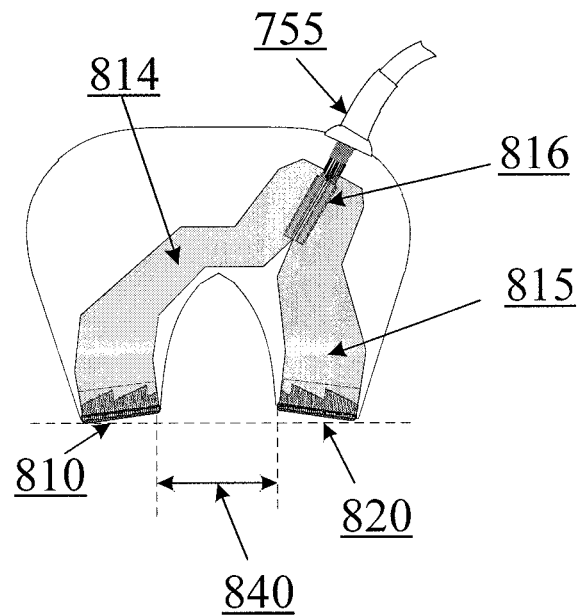
FIG. 8A illustrates an embodiment of the probe of FIG. 8 with internal components visible.

In the embodiment of FIG. 8A, the arrays are shown angled 160 for optimizing beamforming characteristics as discussed above. In some embodiments, the arrays of any of the probes of FIGS. 7-8A may be mounted to respective backing plates similar to those described above for the purpose of securely holding the arrays in a desired position. Such backing plates may be configured to secure and position the arrays at a desired angle, α.

The embodiments shown in FIGS. 9-9B provide a multiple aperture ultrasound Probe for very high resolution imaging by inserting the probe into a body lumen, such as a patient's esophagus. The embodiments of FIGS. 9-9B provide an ultrasound probe that may be mounted to a distal end of an elongate catheter or endoscope configured for positioning and steering the distal probe to a desired position within a body lumen.

FIG. 9 illustrates an embodiment of an Omniplane Style Transesophogeal probe where FIG. 9A is a cut away top view and FIG. 9B is a cut away side view. In this embodiment, an enclosure 940 may contain multiple aperture arrays 910, 920 and 930 that are contained and positioned on a backing plate 992. The backing plate may be mounted on a rotating turn table 982 which can be operated mechanically or electrically to rotate the arrays about an axis perpendicular to the surface of the center array (i.e., an axis perpendicular to the longitudinal axis of the catheter). The enclosure 940 may contain suitable echo-lucent material to facilitate the transfer of ultrasound echo information with a minimum of degradation, and is contained by an acoustic window 950. The operator may manipulate the probe with controls 990 located inside the flex circuit 991. In some embodiments, the flex circuit 991 may be coiled around the arrays allowing the operator to change the arrays' orientation with adequate slack.

In FIG. 9A, the flex circuit 991 is shown terminating into the ends of the elements of each array at 992.

In FIG. 9B, the arrays 910, 920, 930 are shown physically separated from each by a length 980 of a backing block 984. In some such embodiments, each array 910, 920, 930 may have a separate flex connection 992. In some embodiments, coaxial cables may be connected to the common terminal 990 and then placed into a common cable as described above.

Figure 10:
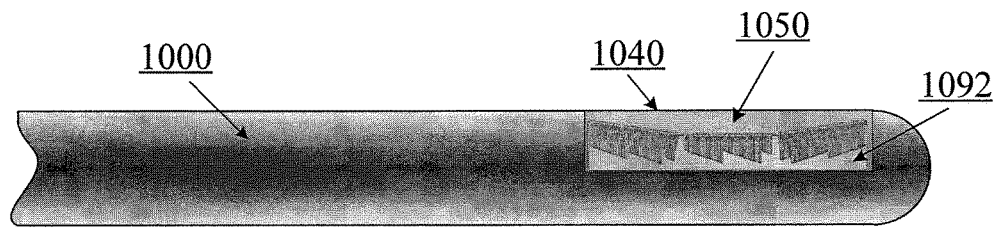
FIG. 10 illustrates an embodiment of a multiple aperture intracavity probe using three arrays with a center array recessed to a point in line with the trailing edges of the outboard arrays with the outboard arrays canted at an angle α. A unified lens may be provided for ease of use as part of the external probe encasement.
Figure 10A:
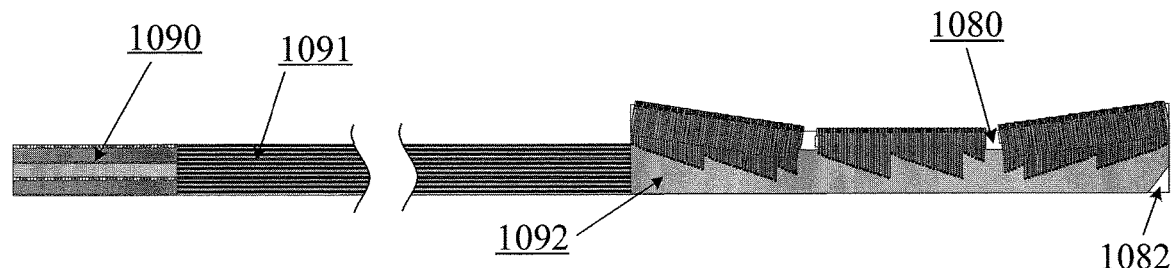
FIG. 10A illustrates a side view of the probe of FIG. 10, showing individual arrays secured and positioned by a backing plate.
Figure 10B:
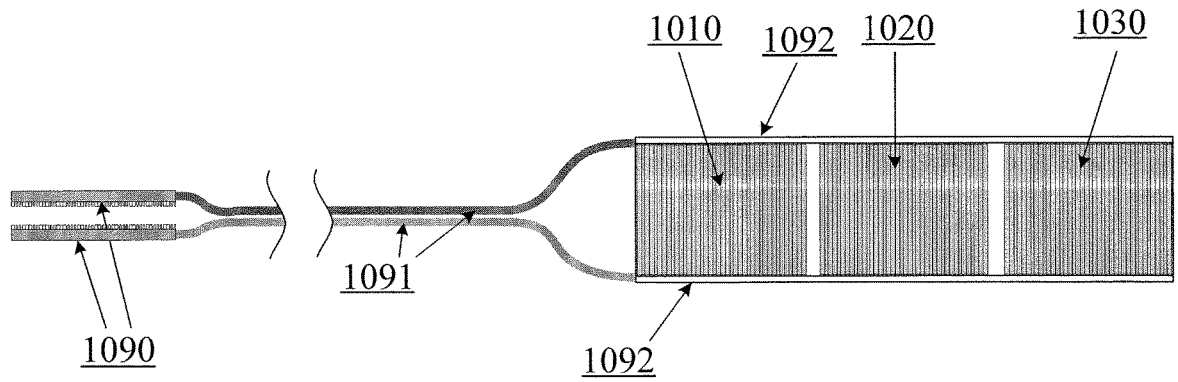
FIG. 10B is a top view of the probe of FIG. 10, showing three arrays and associated cabling internal to an intracavity probe without the encasement.

FIG. 10 illustrates an embodiment of an intracavity probe where FIG. 10A is a cut away side view and FIG. 10B is a cut away top view. In some embodiments, an enclosure 1000 may contain multiple aperture arrays 1010, 1020 and 1030 that are captured and positioned by a backing plate 1082. The enclosure 1000 may contain suitable echo-lucent material 1050 to facilitate the transfer of ultrasound echo information with a minimum of degradation, and may be contained by an acoustic window 1040.

As shown in FIG. 10A, the arrays may be physically separated from each other and held in the shown position by a backing plate 1082. In some embodiments, each array may have a separate flex circuit 1092. The flex circuit 1092 may extend the length of the enclosure 1000 until the flex circuit 1092 reaches the flex/PC board 1090. Coaxial cables extending from a connector may be connected to the flex/PC board 1090. The flex circuits and the coaxial cable may be connected via the flex/PC board in the enclosure.

As shown in FIG. 10B, the flex circuit 1091 may into the ends of each array's elements at 1092.

Figure 11:
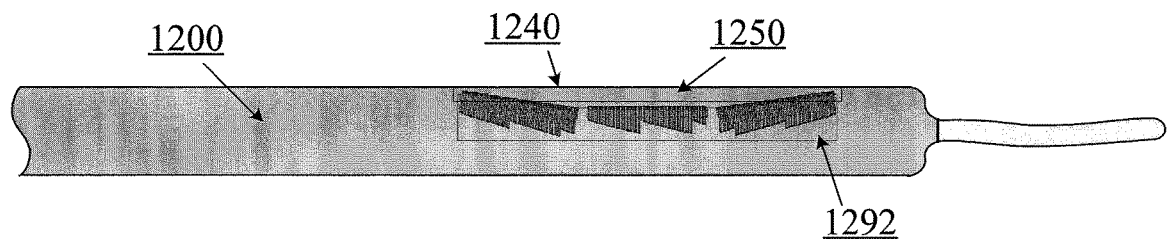
FIG. 11 is a side view of an embodiment of a multiple aperture intravenous ultrasound probe (IVUS) with three arrays where the center array is recessed from a point in line with the trailing edges of the outboard arrays with the outboard arrays canted at an angle α. A unified lens may be provided as part of the external probe encasement.
Figure 11A:
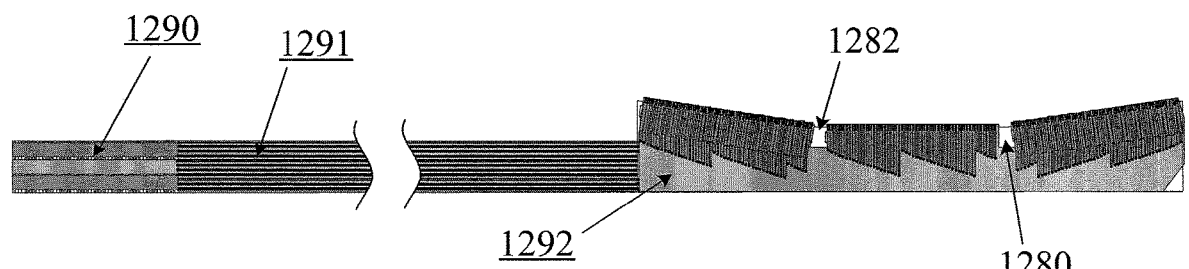
FIG. 11A illustrates a side view of the probe of FIG. 11 showing individual arrays secured and positioned by a backing plate.
Figure 11B:
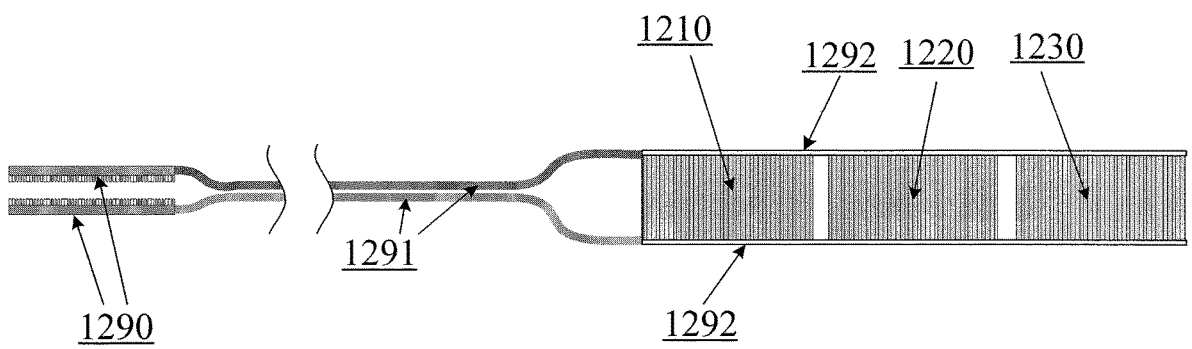
FIG. 11B is a top view of the probe of FIG. 11, showing associated cabling internal to the IVUS probe without the encasement.

FIG. 11 illustrates an embodiment of an Intravenous Ultrasound (IVUS) probe where FIG. 11A is a cut away side view and FIG. 11B is a cut-away top view. In this embodiment, an enclosure 1200 contains multiple aperture arrays 1210, 1220 and 1230 that are captured and positioned by a backing plate 1282. The enclosure 1200 may contain suitable echo-lucent material 1250 to facilitate the transfer of ultrasound echo information with a minimum of degradation, and may be contained by an acoustic window 1240.

As shown in FIG. 11A, the arrays may be physically separated from each other and held in the shown position by a backing plate 1282. In some embodiments, each array may have a separate flex circuit 1292. The flex circuit may extend the length of the enclosure until it reaches the flex/PC board 1290. Coaxial cables extending from a connector may be connected to the flex/PC board 1290. The flex circuits and the coaxial cable may be connected to one another via the flex/PC board in the enclosure.

In FIG. 11B, the flex circuit 1291 is shown terminating into the ends of each array's elements at 1292.

Figure 12:
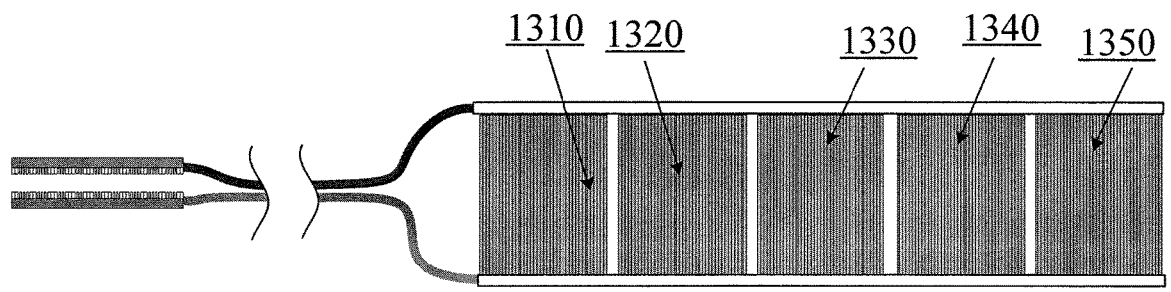
FIG. 12 illustrates a top view of an embodiment of a five array ultrasound probe.
Figure 12A:
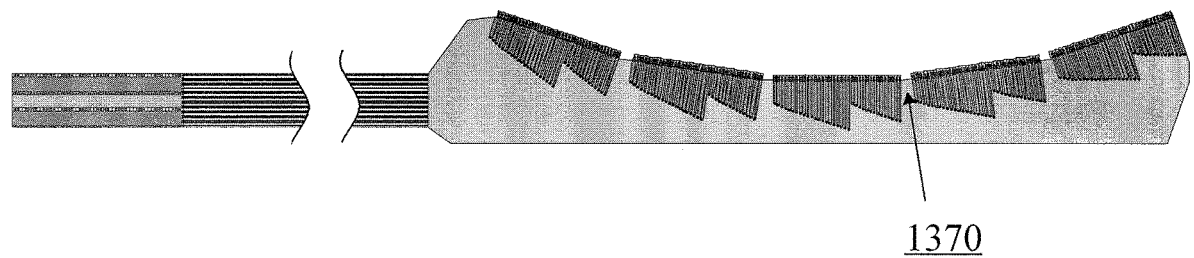
FIG. 12A illustrates a side view of an embodiment of a multiple aperture probe with five arrays.

FIGS. 12-12A illustrates an embodiment of a multiple aperture probe configuration having five arrays 1310, 1320, 1330, 1340 and 1350 that could be used in many of the probes above. While there are five arrays demonstrated here, other embodiments may be configured to utilize more or fewer than five arrays. The number, size, spacing and orientation of the arrays in a particular embodiment may vary depending upon the target application of the probe. Arrays can be as small as an individual element (similar to a pedoff probe) and as large as a matrixed array that covers an entire body cavity. Consequently, arrays need not be positioned within the same transducer housing, furthering the benefits from accurate cable assemblies.

There also is no specific distance 1370 that must separate elements or arrays. The constraints of a symmetrical probe design are diminished by the greater flexibility in array placement enabled by embodiments of the present invention.

Terms such as "optimized," "optimum," "precise," "exact" and similar terms used in relation to quantitative parameters are merely intended to indicate design parameters which may be controlled or varied in accordance with general engineering principles. Use of these terms is not intended to imply or require that the parameters or components thereof are designed for the best possible or theoretical performance.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

What is claimed is:

1. A multiple aperture ultrasound imaging system, comprising:
   an imaging control system containing control electronics;
   an ultrasound probe connected to the imaging control system comprising:
     a probe housing containing a first array of ultrasound transducer elements and a second array of ultrasound transducer elements, the probe housing further comprising a PC board comprising a signal terminal and a ground terminal corresponding to each individual ultrasound transducer element of the first and second arrays, the probe housing further comprising a first flex circuit having a plurality of differential pairs of signal and ground conductors, each differential pair of the first flex circuit connecting one ultrasound transducer element of the first array to its corresponding signal and ground terminals on the PC board;
     wherein each transducer element of the first array and the second array is electrically connected to the imaging control system with a differential pair of conductors, each differential pair having a signal conductor and a ground conductor and being different than another differential pair.

2. The system of claim 1, wherein the probe housing further comprises a backing plate electrically connected to the imaging control system via a chassis ground conductor, wherein the chassis ground conductor is electrically separated from the differential pairs of conductors of the first array and the second array.

3. The system of claim 2, wherein an interior surface of the probe housing comprises a continuous electrically conductive layer electrically connected to the chassis ground conductor.

4. The system of claim 2, wherein the first and second arrays are mechanically secured to the backing plate.

5. The system of claim 1, the probe housing further comprising a second flex circuit having a plurality of differential pairs of signal and ground conductors, each differential pair of the second flex circuit connecting one ultrasound transducer element of the second array to its corresponding signal and ground terminals on the PC board.

6. The system of claim 5, further comprising first and second groups of coaxial cables comprising a plurality of coaxial signal and ground conductors, the first and second groups of coaxial cables being configured to connect the signal and ground terminals of the PC board corresponding to the transducer elements of the first and second ultrasound arrays to the imaging controller with the coaxial signal and ground conductors of the first and second groups of coaxial cables.

7. The system of claim 2, wherein the backing plate internally supports the probe housing.

8. The system of claim 1, the probe housing further comprising a calibration chip mounted on the PC board.

9. The system of claim 8, wherein the calibration chip is configured to store position and orientation information about the first and second ultrasound arrays.

10. The system of claim 1, the probe housing further comprising a probe position sensor mounted on the PC board.

11. The system of claim 5, the probe housing further comprising:
a third ultrasound array of transducer elements secured to the backing plate;
a third flex circuit comprising a plurality of differential pairs of signal and ground conductors, the third flex circuit being configured to connect each transducer element of the third ultrasound array to its corresponding signal and ground terminals of the PC board with one of the differential pairs of signal and ground conductors; and
a third group of coaxial cables comprising a plurality of differential coaxial signal and ground conductors, the third group of coaxial cables being configured to connect the signal and ground terminals of the PC board corresponding to the transducer elements of the third ultrasound array to the imaging controller with the differential coaxial signal and ground conductors of the third group of coaxial cables.

12. The system of claim 1 wherein at least one of the first ultrasound array and the second ultrasound array comprises an internal flex cabling configured to accommodate movement of the first ultrasound array away from the second ultrasound array.

13. The system of claim 1, wherein at least one of the first ultrasound array and the second ultrasound array is configured to rotate about an axis of the probe housing.

14. The system of claim 12, the probe housing further comprising a lever configured to move the first ultrasound array or the second ultrasound array relative to the probe housing.

15. The system of claim 12, the probe housing further comprising a dial and an electric motor configured to move the first ultrasound array or the second ultrasound array relative to the probe housing.

16. The system of claim 1, further comprising an electronic switch on the PC board configured to allow for dynamic switching between the more than one transducer element of the first ultrasound array.

* * * * *